US012570683B2

(12) United States Patent
Gao et al.

(10) Patent No.: US 12,570,683 B2

(45) Date of Patent: Mar. 10, 2026

(54) POLYMORPHIC FORM OF REDUCED BETA-NICOTINAMIDE MONONUCLEOTIDE DISODIUM SALT, AND PREPARATION METHOD THEREFOR AND USE THEREOF

(71) Applicant: EFFEPHARM (SHANGHAI) CO., LTD., Shanghai (CN)

(72) Inventors: Xing Gao, Shanghai (CN); Jianjun Yu, Shanghai (CN); Qiang Shen, Shanghai (CN); Qinyuan Xu, Shanghai (CN); Yinshan Li, Shanghai (CN); Jialing Liu, Shanghai (CN); Liulei Chang, Shanghai (CN)

(73) Assignee: EFFEPHARM (SHANGHAI) CO., LTD., Shanghai (CN)

( * ) Notice: Subject to any disclaimer, the term of this patent is extended or adjusted under 35 U.S.C. 154(b) by 34 days.

(21) Appl. No.: 18/840,839

(22) PCT Filed: Feb. 9, 2023

(86) PCT No.: PCT/CN2023/075226

§ 371 (c)(1),
(2) Date: Aug. 22, 2024

(87) PCT Pub. No.: WO2023/160405

PCT Pub. Date: Aug. 31, 2023

(65) Prior Publication Data

US 2025/0163092 A1 May 22, 2025

(30) Foreign Application Priority Data

Feb. 23, 2022 (CN) ......................... 202210168280.1

(51) Int. Cl.
*C07H 19/048* (2006.01)

(52) U.S. Cl.
CPC .................................. *C07H 19/048* (2013.01)

(58) Field of Classification Search
CPC .......................... C07H 19/048; C07B 2200/13
See application file for complete search history.

(56) References Cited

FOREIGN PATENT DOCUMENTS

| | | | |
|---|---|---|---|
| CN | 107613990 | A | 1/2018 |
| CN | 110845548 | A | 2/2020 |
| CN | 112538101 | A | 3/2021 |
| CN | 113292619 | A | 8/2021 |
| CN | 113490676 | A | 10/2021 |
| CN | 115368423 | A | 11/2022 |
| JP | 2021524865 | A | 9/2021 |
| WO | 2021098725 | A1 | 5/2021 |

OTHER PUBLICATIONS

Ansari, Hifzur R. et al. "Identification of NAD interacting residues in proteins"; BMC Bioinformatics; Mar. 30, 2010; vol. 11, No. 160; pp. 1-8.

Rajman, Luis et al. "Therapeutic Potential of NAD-Boosting Molecules: The In Vivo Evidence"; Cell Metabolism; Mar. 6, 2018; vol. 27, No. 3; pp. 529-547.

Stein, Liana Roberts et al. "The Dynamic Regulation of NAD Metabolism in Mitochondria"; Trends in Endocrinology & Metabolism Impact Factor; Sep. 2012; vol. 23, No. 9; pp. 420-428.

Cantó, Carles et al. "The NAD+ Precursor Nicotinamide Riboside Enhances Oxidative Metabolism and Protects against High-Fat Diet-Induced Obesity"; Cell Metabolism; Jun. 6, 2012; vol. 15, No. 6; pp. 838-847.

Mills, Kathryn F. et al. "Long-Term Administration of Nicotinamide Mononucleotide Mitigates Age-Associated Physiological Decline in Mice"; Cell Metabolism; Dec. 13, 2016; vol. 24, No. 6; pp. 795-806.

Cantó, Carles et al. "NAD+ Metabolism and the Control of Energy Homeostasis: A Balancing Act between Mitochondria and the Nucleus"; Cell Metabolism; Jul. 7, 2015; vol. 22, No. 1; pp. 31-53.

Chiarugi, Alberto et al. "The NAD metabolome—a key determinant of cancer cell biology"; Nature Reviews Cancer; Sep. 28, 2012; vol. 12; pp. 1-12.

Johnson, Sean et al. "NAD+ biosynthesis, aging, and disease [version 1; referees: 2 approved]"; F1000 Research; Feb. 1, 2018; vol. 7; pp. 1-10.

Ashizawa, Kazuhide, Polymorphism and crystallization of the pharmaceutical drugs, Maruzen Planet, Sep. 20, 2002, pp. 273, 278, 305-317, ISBN4901689061.

American Chemical Society. "RN 108347-85-9"; Registry; May 30, 1987; pp. 1.

Liu, Yan et al. "Reduced Nicotinamide Mononucleotide (NMNH) Potently Enhances NAD+ and Suppresses Glycolysis, the TCA Cycle, and Cell Growth"; Journal of Proteome Research; Apr. 1, 2021; vol. 20, No. 5; pp. 2596-2606.

Liu, Yao et al. "Engineering the Biomimetic Cofactors of NMNH for Cytochrome P450 BM3 Based on Binding Conformation Refinement"; RSC Advances; Mar. 24, 2021; vol. 11, No. 20; pp. 12036-12042.

Zapata-Pérez, Rubén et al., "Reduced nicotinamide mononucleotide is a new and potent NAD+ precursor in mammalian cells and mice", The FASEB Journal, Apr. 2021, vol. 25, No. 4, pp. 1-17.

Byrn, Stephen et al., "Pharmaceutical Solids: A Strategic Approach to Regulatory Considerations", Pharmaceutical Research, Jul. 1995, vol. 12, No. 7, pp. 945-954.

(Continued)

*Primary Examiner* — Layla D Berry

(74) *Attorney, Agent, or Firm* — NKL Law; Bin Lu; Allen Xue

(57) ABSTRACT

A polymorph of a reduced β-nicotinamide mononucleotide disodium salt, and a preparation method therefor and the use thereof as a pharmaceutical ingredient, a healthcare product ingredient, a cosmetic ingredient, or a food additives, and a preparation containing the salts are provided. A polymorph of NMNH disodium salt has excellent solubility, stability, flow performance, and hygroscopicity resistance. Its purification effects is better than that of amorphous forms.

14 Claims, 15 Drawing Sheets

(56) References Cited

OTHER PUBLICATIONS

Bastin, Richard J. et al., "Salt Selection and Optimisation Procedures for Pharmaceutical New Chemical Entities", Organic Process Research & Development, Jul. 19, 2000, vol. 4, No. 5, pp. 427-435.

POLYMORPHIC FORM OF REDUCED BETA-NICOTINAMIDE MONONUCLEOTIDE DISODIUM SALT, AND PREPARATION METHOD THEREFOR AND USE THEREOF

TECHNICAL FIELD

The present invention relates to the field of chemical raw materials for pharmaceuticals, healthcare product and cosmetics, and specifically relates to the polymorphic forms of reduced β-nicotinamide mononucleotide disodium salts, and preparation method therefor and use thereof.

BACKGROUND TECHNOLOGY

Nicotinamide adenine dinucleotide ($NAD^+$), one of the hottest molecules in the field of anti-aging, is without exception at the center of successive generations of anti-aging substances. $NAD^+$ is an essential coenzyme required for over 500 enzymatic reactions and is well known for its role in oxidation and reduction (Ansari and Raghava, 2010; Rajman et al. 2018; Stein and Imai, 2012). A growing number of studies have instructed that increasing $NAD^+$ equivalents significantly improves multiple organ functions, including liver function, kidney function, heart function and skeletal muscle function (Canto et al. 2012; Mills et al. 2016; Rajman et al., 2018). $NAD^+$ can be synthesized using tryptophan in the de novo biosynthesis pathway (de novo biosynthesis pathway), nicotinic acid (NA) in the preiss-handler pathway, as well as nicotinamide (NAM), nicotinamide riboside (NR), and nicotinamide mononucleotide (NMN) in the salvage pathway (Canto et al. 2015; Chiarugi et al. 2012; Johnson and Imai 2018). In particular, as key intermediates of $NAD^+$, NAM, NR, and NMN have been extensively studied for their potential therapeutic roles in many mouse disease models (Mills et al., 2016), wherein NMN is considered to be the most suitable $NAD^+$ precursor at present, and NMN is currently hotly sold in the global marketplace and is highly favored by consumers.

NMNH (molecular structure as shown in formula (A)), known as "reduced nicotinamide mononucleotide" or "reduced β-nicotinamide mononucleotide" in Chinese, is a reduced form of NMN. NMNH is a new precursor for $NAD^+$ supplementation with better $NAD^+$-promoting effects than NMN, as well as other biological functions such as increasing cellular antioxidant capacity, reducing fat accumulation, reducing inflammatory response and inhibiting tumor cell growth, etc., and is a health-promoting reagent with significant commercial potential (WO2021098725A1).

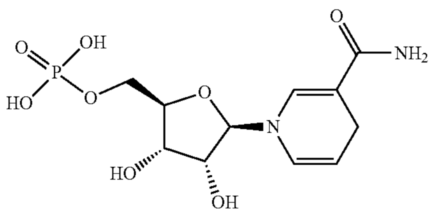

NMNH
(A)

The synthesis process of NMNH in the market is still in the laboratory research and development stage, and it is not yet possible to realize industrial production. The main technical difficulties in the synthesis of NMNH are: 1) NMNH is a reduced form of NMN, which is easily oxidized by air; 2) In the laboratory, an aqueous solution with higher purity can be obtained only by preparative chromatography, and an amorphous solid can be obtained by freeze-drying. This method has no purification effect on the product, and the amorphous solid obtained by freeze-drying is foamy, has poor fluidity, is easy to absorb moisture and becomes oil, and degrades quickly; 3) No polymorphic form has been reported. It is well known that freeze-drying is not used industrially unless it is necessary because of its high energy consumption and limited production capacity; amorphous solids have higher energy and are more unstable than crystalline solids.

Therefore, there is an urgent need in this field to develop new NMNH compounds and polymorphic form thereof with advantages of good stability, good fluidity and suitability for industrialization.

SUMMARY OF THE INVENTION

The purpose of the present invention is to provide new NMNH compounds and polymorphic forms thereof, namely polymorphic forms of NMNH disodium salts and preparation method therefor and the uses thereof, which have the advantages of good stability, good fluidity and suitability for industrialization.

A first aspect of the present invention provides crystals of a reduced β-nicotinamide mononucleotide disodium salt, and the crystal form of the crystals is selected from the group consisting of: crystal form A, crystal form B, and crystal form C.

In another preferred embodiment, the structure of the reduced β-nicotinamide mononucleotide disodium salt is shown in Formula I:

(I)

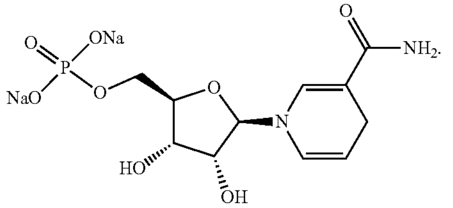

In another preferred embodiment, the crystals of reduced β-nicotinamide mononucleotide disodium salt are hydrate.

In another preferred embodiment, the structure of the reduced β-nicotinamide mononucleotide disodium salt is shown in Formula II (II)

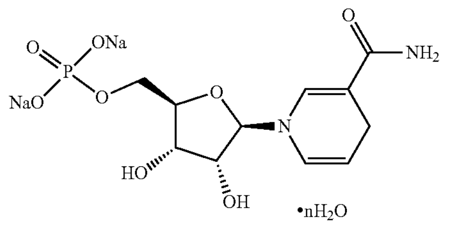

where n is ≥2.

In another preferred embodiment, n is an integer or a non-integer.

In another preferred embodiment, n is a positive integer of ≥2, preferably 2-10, more preferably 5-9.

In another preferred embodiment, the XRPD pattern of the crystal form A comprises 3 or more 2θ values selected from the group consisting of: 12.7°±0.2°, 15.9°±0.2°, 18.0°±0.2°, 20.4°±0.2°, 20.9°±0.2°, and 31.8°±0.2°.

In another preferred embodiment, the XRPD pattern of the crystal form A comprises 1 or more 2θ values selected from the group consisting of: 10.5°±0.2°, 19.8°±0.2°, 22.6°±0.2°, 24.0°±0.2°, 26.1°±0.2°, 28.7°±0.2°, 30.8°±0.2°, and 33.4°±0.2°.

In another preferred embodiment, the crystal form A further has one or more features selected from the following group:

1) the XRPD pattern of the crystal form A comprises 6 or more 2θ values selected from the group consisting of: 5.0°±0.2°, 10.5°±0.2°, 12.7°±0.2°, 13.7°±0.2°, 14.9°±0.2°, 15.9°±0.2°, 16.1°±0.2°, 16.6°±0.2°, 18.0°±0.2°, 19.8°±0.2°, 20.4°±0.2°, 20.9°±0.2°, 22.6°±0.2°, 24.0°±0.2°, 24.7°±0.2°, 25.2°±0.2°, 25.7°±0.2°, 26.1°±0.2°, 27.8°±0.2°, 28.7°±0.2°, 29.3°±0.2°, 30.3°±0.2°, 30.8°±0.2°, 31.8°±0.2°, 32.7°±0.2°, 33.4°±0.2°, 34.2°±0.2°, 35.8°±0.2°, 36.4°±0.2°, 37.4°±0.2°, 39.7°±0.2°, 41.2°±0.2°, 41.7°±0.2°, 42.6°±0.2°, 43.9°±0.2°, 44.3°±0.2°, 46.0°±0.2°, 46.4°±0.2°, and 49.2°±0.2°;
2) the XRPD pattern of the crystal form A is substantially as characterized in FIG. 1;
3) the TGA pattern of the crystal form A has a weight loss of 19%-30% at 15° C.-200° C.;
4) the TGA pattern of the crystal form A is substantially as characterized in FIG. 2;
5) the DSC pattern of the crystal form A has a heat absorption peak in the range of 50° C.-80° C.;
6) the DSC pattern of the crystal form A is substantially as characterized in FIG. 3;
7) the crystal form A is pentahydrate, hexahydrate, heptahydrate, octahydrate, or nonahydrate.

In another preferred embodiment, the crystal form B has one or more features selected from the following group:

1) the XRPD pattern of the crystal form B comprises 3 or more 2θ values selected from the group consisting of: 12.0°±0.2°, 14.5°±0.2°, 15.3°±0.2°, 17.5°±0.2°, 19.9°±0.2°, and 21.5°±0.2°;
2) the XRPD pattern of the crystal form B comprises 1 or more 2θ values selected from the group consisting of: 21.1°±0.2°, 23.1°±0.2°, and 25.5°±0.2°;
3) the XRPD pattern of the crystal form B comprises 6 or more 2θ values selected from the group consisting of: 5.2°±0.2°, 7.7°±0.2°, 10.5°±0.2°, 11.5°±0.2°, 12.0°±0.2°, 12.6°±0.2°, 13.7°±0.2°, 14.5°±0.2°, 15.3°±0.2°, 16.5°±0.2°, 17.1°±0.2°, 17.5°±0.2°, 18.5°±0.2°, 19.4°±0.2°, 19.9°±0.2°, 21.1°±0.2°, 21.5°±0.2°, 22.5°±0.2°, 23.1°±0.2°, 24.1°±0.2°, 24.7°±0.2°, 25.5°±0.2°, 26.4°±0.2°, 27.2°±0.2°, 27.7°±0.2°, 28.3°±0.2°, 29.2°±0.2°, 29.5°±0.2°, 31.2°±0.2°, 32.1°±0.2°, 32.6°±0.2°, 34.2°±0.2°, 35.1°±0.2°, 36.6°±0.2°, 38.3°±0.2°, 39.7°±0.2°, 41.4°±0.2°, 43.0°±0.2°, 45.1°±0.2°, and 45.7°±0.2°;
4) the XRPD pattern of the crystal form B is substantially as characterized in FIG. 4;
5) the TGA pattern of the crystal form B has a weight loss of 12%-23% at 15° C.-200° C.;
6) the TGA pattern of the crystal form B is substantially as characterized in FIG. 5;
7) the DSC pattern of the crystal form B has a heat absorption peak in the range of 50° C.-80° C.;
8) the DSC pattern of the crystal form B is substantially as characterized in FIG. 6;
9) the crystal form B is trihydrate, tetrahydrate, pentahydrate, or hexahydrate.

In another preferred embodiment, the crystal form C has one or more features selected from the following group:

1) the XRPD pattern of the crystal form C comprises 3 or more 2θ values selected from the group consisting of: 6.3°±0.2°, 15.3°±0.2°, 17.7°±0.2°, 19.9°±0.2°, 20.2°±0.2°, and 21.5°±0.2°;
2) the XRPD pattern of the crystal form C comprises 1 or more 2θ values selected from the group consisting of: 6.3°±0.2°, 10.0°±0.2°, 12.1°±0.2°, 12.3°±0.2°, 12.8°±0.2°, 15.3°±0.2°, 16.6°±0.2°, 17.7°±0.2°, 19.9°±0.2°, 20.2°±0.2°, 21.5°±0.2°, 23.3°±0.2°, 24.9°±0.2°, 25.6°±0.2°, and 33.7θ±0.2°;
3) the XRPD pattern of the crystal form C is substantially as characterized in FIG. 7;
4) the TGA pattern of the crystal form C has a weight loss of 8%-16% at 15° C.-200° C.;
5) the TGA pattern of the crystal form C is substantially as characterized in FIG. 8;
6) the DSC pattern of the crystal form C has a heat absorption peak in the range of 50° C.-80° C.;
7) the DSC pattern of the crystal form C is substantially as characterized in FIG. 9;
8) the crystal form C is dihydrate, trihydrate, or tetrahydrate.

A second aspect of the present invention provides a method for preparing crystals of reduced β-nicotinamide mononucleotide disodium salt, the method comprises the following steps:

1) The reduced β-nicotinamide mononucleotide disodium salt was added to the first solvent to obtain a solution containing reduced β-nicotinamide mononucleotide disodium salt;
2) Under stirring conditions, to the solution was added dropwise a second solvent, and crystallized to obtain the crystal of the reduced β-nicotinamide mononucleotide disodium salt; alternatively, under stirring conditions, the solution was purged with nitrogen, and crystallized to obtain the crystal of the reduced β-nicotinamide mononucleotide disodium salt, alternatively, under stirring conditions, the solution was concentrated under reduced pressure, and crystallized to obtain the crystal of the reduced β-nicotinamide mononucleotide disodium salt.

In another preferred embodiment, the first solvent and the second solvent are the same or different, and are independently selected from the group consisting of: water, acetonitrile, tetrahydrofuran, methyl tert-butyl ether, 2-methyltetrahydrofuran, dichloromethane, N,N-dimethylformamide, N,N-dimethylacetamide, N,N-diethylformamide, dimethylsulfoxide, ethyl acetate, isopropyl acetate, ketone solvent, alcohol solvent, or a combination thereof.

In another preferred embodiment, the ketone solvent is selected from the group consisting of: acetone, 2-butanone, methyl isobutyl ketone, methyl tert-butyl ketone, 3-methyl-2-butanone, or a combination thereof.

In another preferred embodiment, the alcohol solvent is selected from the group consisting of: methanol, ethanol, n-propanol, isopropanol, n-butanol, isobutanol, n-amyl alcohol.

In another preferred embodiment, the method further comprises: step 3), drying the crystals.

In another preferred embodiment, the drying comprises: drying the resulting crystals under vacuum for 2-30 hours In another preferred embodiment, the crystal is crystal form A.

In another preferred embodiment, when the crystals obtained in step 2) are crystal form B and/or crystal form C, then the step 2) further comprises a sub-step 2a), wherein the crystal form B and/or the crystal form C are placed in a moisture-containing gas and thus converted to crystal form A.

In another preferred embodiment, in step 2a), crystal form B and/or crystal form C are placed in air and thus converted to crystal form A.

A third aspect of the present invention provides a composition, the composition comprises: (a) any of the crystals described in the first aspect, and (b) pharmaceutically acceptable excipients or carriers, acceptable excipients or carriers for healthcare product, acceptable excipients or carriers for cosmetic, or acceptable excipients or carriers for food.

In another preferred embodiment, the composition is selected from the group consisting of: pharmaceutical compositions, healthcare product compositions, cosmetic compositions, or food compositions.

In another preferred embodiment, the pharmaceutical composition comprises (a) any of the crystals described in the first aspect, and (b) pharmaceutically acceptable excipients or carriers.

In another preferred embodiment, the dosage form of the pharmaceutical composition is selected from the group consisting of: oral formulation, injectable dosage form, respiratory delivery dosage form, dermal delivery dosage form, mucosal delivery dosage form, luminal delivery dosage form and the like.

In another preferred embodiment, the healthcare product composition comprises (a) any of the crystals described in the first aspect, and (b) acceptable excipients or carriers for healthcare product.

In another preferred embodiment, the cosmetic composition comprises (a) any of the crystals described in the first aspect, and (b) acceptable excipients or carriers for cosmetic.

In another preferred embodiment, the cosmetic composition comprises a cosmetic of use selected from the group consisting of: skin cosmetic, hair cosmetic, beauty cosmetic, special function cosmetic.

In another preferred embodiment, the food composition comprises (a) any of the crystals described in the first aspect, and (b) acceptable excipients or carriers for food.

A fourth aspect of the present invention provides the use of a crystal in the preparation of a drug or a healthcare product or a cosmetic or a food additive.

In another preferred embodiment, the drug is used for protecting the optic nerve, improving retinal damage, preventing/treating hair loss, preventing/improving cardiovascular and cerebrovascular diseases, inhibiting renal tubular damage and aging, preventing hepatic fibrosis, improving fatty liver disease, improving symptoms of dry eye, repairing renal damage, preventing diabetes/nephropathy, improving symptoms of sarcopenia in the elderly, treating chronic inflammation, alleviating condition of polycystic ovary syndrome patients, preventing/delaying glaucoma, reducing neuroinflammation, reducing cardiotoxicity of anthracycline chemotherapy drugs, aiding recovery from cerebral infarction, and combating heart failure in the elderly.

In another preferred embodiment, the healthcare product are used for slowing down cellular aging, slowing down reproductive aging in females, improving fertility, improving menopause, enhancing male sexual function, improving sleep, soothing mood, boosting energy, improving cardiovascular function, boosting cardiovascular health, boosting immunity, improving sub-health, preventing tumors, preventing Alzheimer's disease, and the like.

In another preferred embodiment, the cosmetic product is used for improving damaged cell function, improving skin/hair texture, preventing/treating photoaging of the skin, maintaining softness and elasticity of the skin, slowing down aging of the skin, and the like.

In another preferred embodiment, the food additive is used for improving appetite, improving digestion, promoting metabolism, promoting hair/nail growth, etc., and enhancing nutritional value.

It should be understood that, within the scope of the present invention, each of the above-described technical features of the present invention and each of the technical features specifically described below (e.g., in the embodiments) can be combined with each other, thereby constituting a new or preferred technical solution. For the sake of limitation of space, we will not repeat all of them herein.

DETAILED DESCRIPTION OF THE INVENTION

Figure 1:
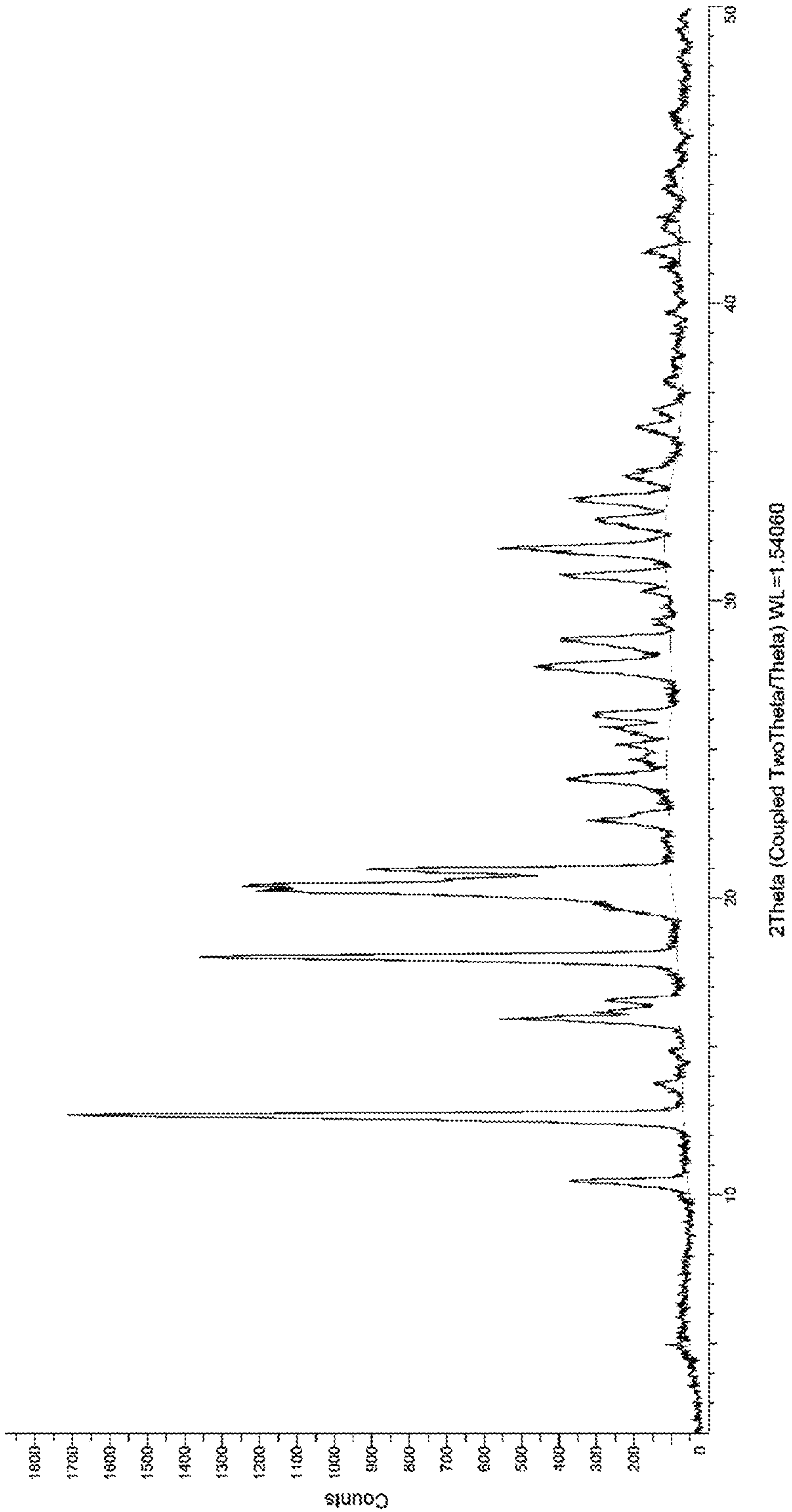
FIG. 1 shows the XRPD pattern of NMNH disodium salt crystal form A.

Through extensive and intensive research, the present inventor has for the first time unexpectedly developed a specific salt of reduced NMNH, and the salt is the disodium salt of NMNH. The studies of the present invention have shown that the polymorphic form (particularly crystal form A) of the disodium salt of NMNH, has excellent stability.

Compared to its amorphous solid, the amorphous form changes from a solid to an oil or viscous mass and degrades rapidly upon placement. In addition, the polymorphic form of the present invention has the advantages of high purity, good stability, good fluidity, and low hygroscopicity, which makes it suitable for use in pharmaceutical compositions, healthcare products, cosmetics, food additives, and the like. On this basis, the inventor has completed the present invention.

Terms

Unless otherwise defined, all technical and scientific terms used herein have the same meaning as commonly understood by those of ordinary skill in the art to which the present invention belongs.

As used herein, n in the term "$nH_2O$" refers to all possible values including integers and non-integers between 2 and 10; "$H_2O$" is the chemical formula for water, representing water molecules or water.

As used herein, when used in reference to a specifically enumerated value, the term "about" means that the value can vary by no more than 1% from the specifically enumerated value, e.g., as used herein, the expression "about 100" includes all values between 99 and 101 (e.g., 99.1, 99.2, 99.3, 99.4, etc.).

As used herein, the terms "contains" or "includes (comprises)" can be open-ended, semi-enclosed and closed-ended. In other words, the terms mentioned also include "substantially consisting of" or "consisting of".

As used herein, the term "n or more 2θ values selected from the group consisting of" means including n and any positive integer greater than n (e.g., n, n+1, . . . ), where the upper limit Nup is the number of all 20 peaks in the group. For example, "3 or more" includes not only 3, 4, 5, 6, 7, 8, 9, 10, 11, 12, 13, 14, 15, 16, 17, 18, 19, 20, 21, . . . each positive integer of the upper Nup, but also "4 or more". or more", "5 or more", "6 or more" and other ranges.

NMNH Disodium Salt

As used herein, the terms "reduced β-nicotinamide mononucleotide disodium salt", "β-dihydronicotinamide mononucleotide disodium salt", "dihydronicotinamide mononucleotide disodium salt", "reduced nicotinamide mononucleotide disodium salt", "reduced NMN disodium salt", and "$NMNH-Na_2$" are used interchangeably, and all refer to the salt formed by reducing β-nicotinamide mononucleotide salt formed with two sodium ions, the structure of which is shown in Formula I. It should be understood that the term includes both hydrates and anhydrates.

(I)

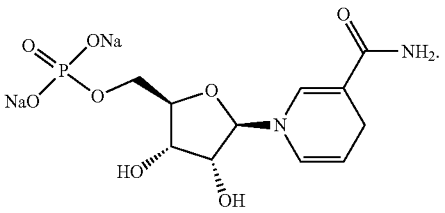

In the present invention, the preferred reduced NMN disodium salt is a hydrate with the structure shown in formula (II):

(II)

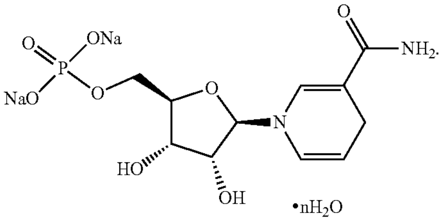

Polymorph

Solids exist either in an amorphous form or in a crystal form. In the case of the crystal form, the molecules are localized in a three-dimensional lattice. When a compound is crystallized from a solution or slurry, it can be crystallized in different spatial point arrangements (this property known as the "polycrystalline phenomenon"), and form crystals with different crystal forms, which are known as "polymorph". Different polymorphs of a given substance may differ from each other in one or more physical properties (e.g., solubility and rate of dissolution, true specific gravity, crystal form, stacking mode, fluidity and/or solid state stability).

The polymorphic form of a compound can exhibit different melting points, hygroscopicity, stability, solubility, bioavailability, bioactivity, and mobility, which are important factors affecting the druggability.

As used herein, "crystals", "crystals of the present invention" or "polymorphs" are used interchangeably to refer to crystals described in the first aspect of the present invention, and the crystal form of which is selected from the following group: crystal form A, crystal form B, or crystal form C.

Crystallization

Production scale crystallization can be accomplished by manipulating the solution such that the solubility limit of the target compound is exceeded. This can be accomplished by a variety of methods, for example, by dissolving the compound at a relatively high temperature and then cooling the solution below the saturation limit. Alternatively, the liquid volume may be reduced by boiling, atmospheric pressure evaporation, vacuum drying, or some other method. The solubility of the target compound may be reduced by adding an anti-solvent or a solvent in which the compound has a low solubility or a mixture of such solvents. Another optional method is to adjust the pH to reduce the solubility. A detailed description of crystallization aspects can be found in Crystallization, Third Edition, J. W. Mullens, Butterworth-Heineman Ltd. 1993, ISBN 0750611294.

If the formation of the desired salt occurs simultaneously with crystallization, and if the salt is less soluble than the feedstock in the reaction medium, then the addition of an appropriate acid or base can lead to the direct crystallization of the desired salt. Similarly, the completion of a synthetic reaction in a medium in which the final desired form is less soluble than the reactants can lead to direct crystallization of the final product.

Optimization of crystallization may include inoculating the crystallization medium with crystals of a desired form as a crystalline seed. Alternatively, many crystallization methods use a combination of the above strategies. One embodiment is to dissolve the target compound in a solvent at elevated temperatures, followed by the addition of an appropriate volume of anti-solvent in a controlled manner to allow the system just below the saturation level. At this point, the seed crystal of a desired form (and the integrity of the seed crystal is maintained) can be added, and the system is cooled to complete crystallization.

Solvate

During the contact between compounds or drug molecules and solvent molecules, it is unavoidable that the solvent molecules and compound molecules form eutectic crystal and thus remain in the solid substance due to the external and internal conditions. The substance formed after crystallization of the compound with the solvent is called solvate. The solvents that can easily form solvates with organic compounds are water, methanol, ethanol, benzene, ether, and heterocyclic aromatic hydrocarbons, etc.

Hydrate

Hydrate is a special kind of solvent. In the pharmaceutical industry, both in the synthesis of APIs, drug formulation, drug storage and the evaluation of drug activity, hydrates are valuable for separate discussion because of their special characteristics.

In the present invention, the crystals of the compound shown in formula (I) can be a non-solvent compound or a solvent compound; the crystal form A, crystal form B, and crystal form C of the crystals of the compound shown in formula (I) are all hydrates.

Preparation Method

In the preparation of NMNH disodium salt crystals of the present invention, temperature-controlled crystallization, decompression concentration crystallization, nitrogen gas blowing crystallization, volatilization crystallization, dissolution and precipitation crystallization, temperature-controlled and humidity-controlled transcrystallization, vacuum drying transcrystallization and so on are used. And the method is simple and easy to industrial production.

Use

The present invention provides the use of NMNH disodium salt crystals (including crystal form A, crystal form B, crystal form C): the crystals are highly efficient and broad-spectrum, and can be used in pharmaceutical compositions, healthcare product, cosmetics, food additives and the like.

The main advantages of the present invention are:

(1) The crystals of the compound of formula (I) of the present invention (including crystal form A, crystal form B, crystal form C), compared with its amorphous solid, have a high purity, a good stability, a good fluidity, and a low hygroscopicity.

(2) The crystal preparation method of the compound of formula (I) of the present invention (including crystal form A, crystal form B, crystal form C) is simple and is more suitable for industrial production than the lyophilization process (which is energy-consuming and has limited production capacity).

(3) The crystals of the compound of formula (I) of the present invention (including crystal form A, crystal form B, crystal form C) can be used in pharmaceutical compositions, healthcare product, cosmetics, food additives and the like.

(4) The preparation methods of polymorphs of the present invention is a simple and suitable for industrialized production.

The present invention is further described below in connection with specific embodiments. It should be understood that these embodiments are used only to illustrate the invention and are not intended to limit the scope of the invention. Experimental methods for which specific conditions are not indicated in the following embodiments are generally in accordance with conventional conditions, or in accordance with conditions recommended by the manufacturer. Percentages and portions are calculated by weight unless otherwise indicated.

Unless otherwise defined, all professional and scientific terms used herein have the same meaning as those familiar to those skilled in the art. In addition, any methods and materials similar or equivalent to those described may be used in the methods of the present invention.

The experimental materials and reagents used in the following examples are available from commercially available sources if not otherwise specified.

Test Methods:

XRPD (X-ray Powder Diffraction) method: Bruker D2 Phaser X-ray Powder Diffractometer; Radiation source C u (1.54060 Å); Generator kv: 30 kv; Generator mA: 10 mA; Starting 2θ: 2.000°; Scanning range: 2.0000-50.000°; Scanning step 0.02°; Scanning speed 0.1 s/step.

Measurement errors associated with the results of this X-ray powder diffraction analysis are generated by a variety of factors including: (a) errors in the sample preparation (e.g., sample height), (b) instrumental errors, (c) calibration differences, (d) operator errors (including errors in determining peak position), and (e) properties of the substance (e.g., preferred orientation errors). Calibration errors and sample height errors often result in displacement of all peaks in the same direction. When using flat holders, small differences in sample height will result in large displacements in XRPD peak positions. Systematic studies have shown that a 1 mm difference in sample height can lead to peak displacements as high as 1° of 2 θ. These displacements can be identified from the XRPD pattern and can be eliminated by either compensating for the displacements (applying the system calibration factor to all peak position values) or recalibrating the instrument. Measurement errors from different instruments can be corrected by applying system calibration factors to make peak positions consistent, as described above.

TGA (thermogravimetric analysis) pattern determination method: TGA55 instrument from TA Company, USA; temperature range: 14.8-300° C.; heating rate: 10° C./min; nitrogen flow rate: 40 mL/min.

DSC (Differential Scanning Calorimetry) pattern determination method: TA Q55 instrument from TA Company, USA; temperature range: 20-230° C., heating rate: 10° C./min, nitrogen flow rate: 50 mL/min.

Moisture (KF) determination method: MC-2000 automatic micro-moisture tester from Min Measure Instrument and Equipment (Xiamen) Co., Ltd. and Karl Fischer reagent from Nanjing Chemical Reagent Co., Ltd.

Example 1. Preparation of Crystal Form A

Preparation of NMNH disodium salt: 179 mg of MnCl2 was added to 2.85 liters of Tris-HCl (50 mM) solution, the pH of the solution was adjusted to 8.0, and the temperature was controlled at 37° C. To the solution was added 143 mg of $NAD^+$ pyrophosphatase from *Escherichia coli* (EcNADD) and 10 g of NADH, and it was stirred for 2 hours. The NMNH solution was separated by preparative chromatography, adjusted to pH=10 with NaOH, and concentrated under reduced pressure to obtain 3.8 g of NMNH disodium salt solid.

500 mg of NMNH disodium salt was weighed and dissolved in 1 ml of water, purged with nitrogen at 20-40° C., crystals were precipitated and filtered, the obtained solid was dried in a blast oven. The crystal form of the resulting solid was crystal form A of the compound of formula (I), and the moisture (KF) was 27%.

Figure 13:
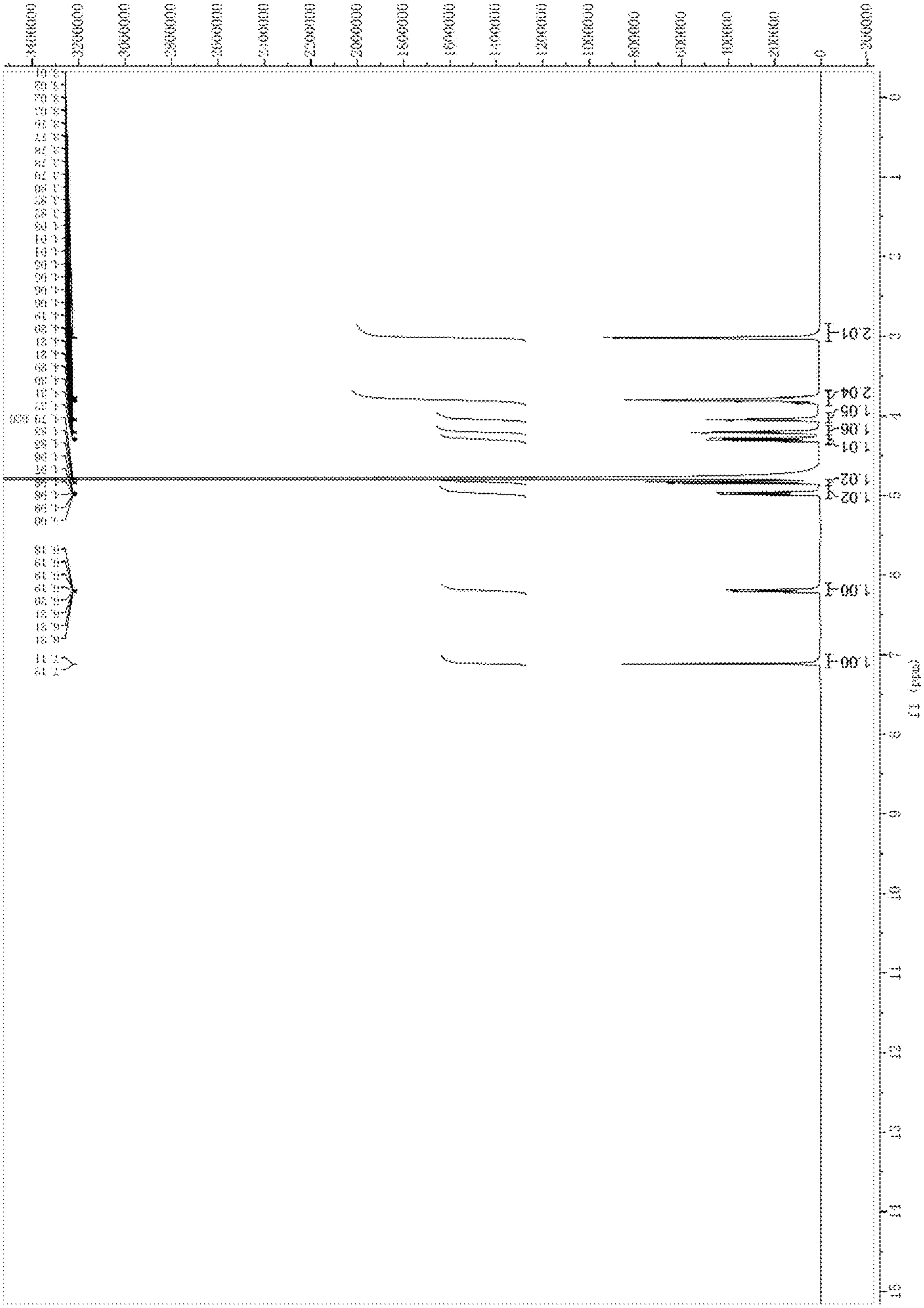
FIG. 13 shows the $^{1}H$ NMR pattern of NMNH disodium salt crystal form A.

X-ray powder diffraction tests were carried out on the resulting solid, and the XRPD pattern of the resulting crystal form A is substantially shown in FIG. 1, the $^1$H NMR pattern is shown in FIG. 13, and the diffraction angle data are substantially shown in Table 1 below, where the error range of the 2θ value is ±0.2°.

TABLE 1

XRPD data for crystal form A

| 2θ (°) | d(Å) | Relative intensity |
|---|---|---|
| 4.97 | 17.75346 | 3.5% |
| 10.49 | 8.42968 | 19.6% |
| 12.69 | 6.96993 | 100.0% |
| 13.72 | 6.45031 | 4.6% |
| 14.86 | 5.95545 | 2.0% |
| 15.94 | 5.55607 | 27.2% |
| 16.14 | 5.48783 | 11.9% |
| 16.55 | 5.35113 | 11.1% |
| 18.02 | 4.91986 | 79.2% |
| 19.79 | 4.48215 | 10.7% |
| 20.41 | 4.34730 | 69.0% |
| 20.92 | 4.24317 | 47.0% |
| 22.60 | 3.93079 | 12.9% |
| 24.00 | 3.70484 | 15.4% |
| 24.66 | 3.60803 | 6.3% |
| 25.16 | 3.53612 | 8.5% |
| 25.69 | 3.46436 | 8.7% |
| 26.13 | 3.40740 | 12.9% |
| 27.78 | 3.20916 | 22.2% |
| 28.66 | 3.11191 | 16.8% |
| 29.31 | 3.04460 | 2.1% |
| 30.30 | 2.94746 | 4.6% |
| 30.83 | 2.89811 | 17.0% |
| 31.77 | 2.81429 | 26.5% |
| 32.70 | 2.73667 | 10.3% |
| 33.40 | 2.68027 | 14.3% |
| 34.18 | 2.62097 | 7.1% |
| 35.82 | 2.50471 | 6.2% |
| 36.40 | 2.46626 | 4.2% |
| 37.41 | 2.40230 | 2.5% |
| 39.69 | 2.26888 | 1.9% |
| 41.22 | 2.18824 | 2.9% |
| 41.72 | 2.16322 | 4.5% |
| 42.63 | 2.11907 | 2.9% |
| 43.87 | 2.06223 | 3.2% |
| 44.32 | 2.04205 | 2.2% |
| 45.98 | 1.97234 | 2.0% |
| 46.42 | 1.95466 | 1.7% |
| 49.20 | 1.85061 | 2.1% |

Figure 2:
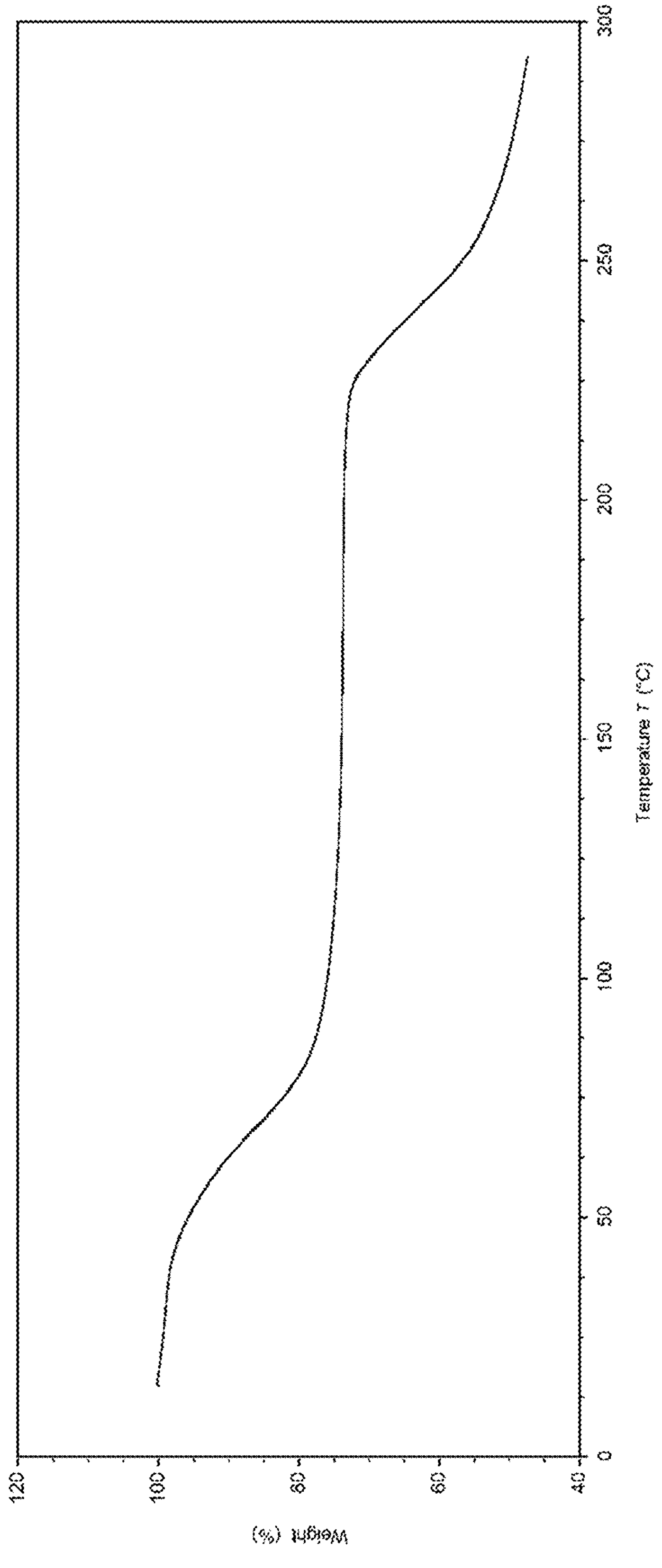
FIG. 2 shows the TGA pattern of NMNH disodium salt crystal form A.

The TGA pattern of crystal form A is substantially as shown in FIG. 2, with a weight loss of 19%-30% at 15° C.-200° C.

Figure 3:
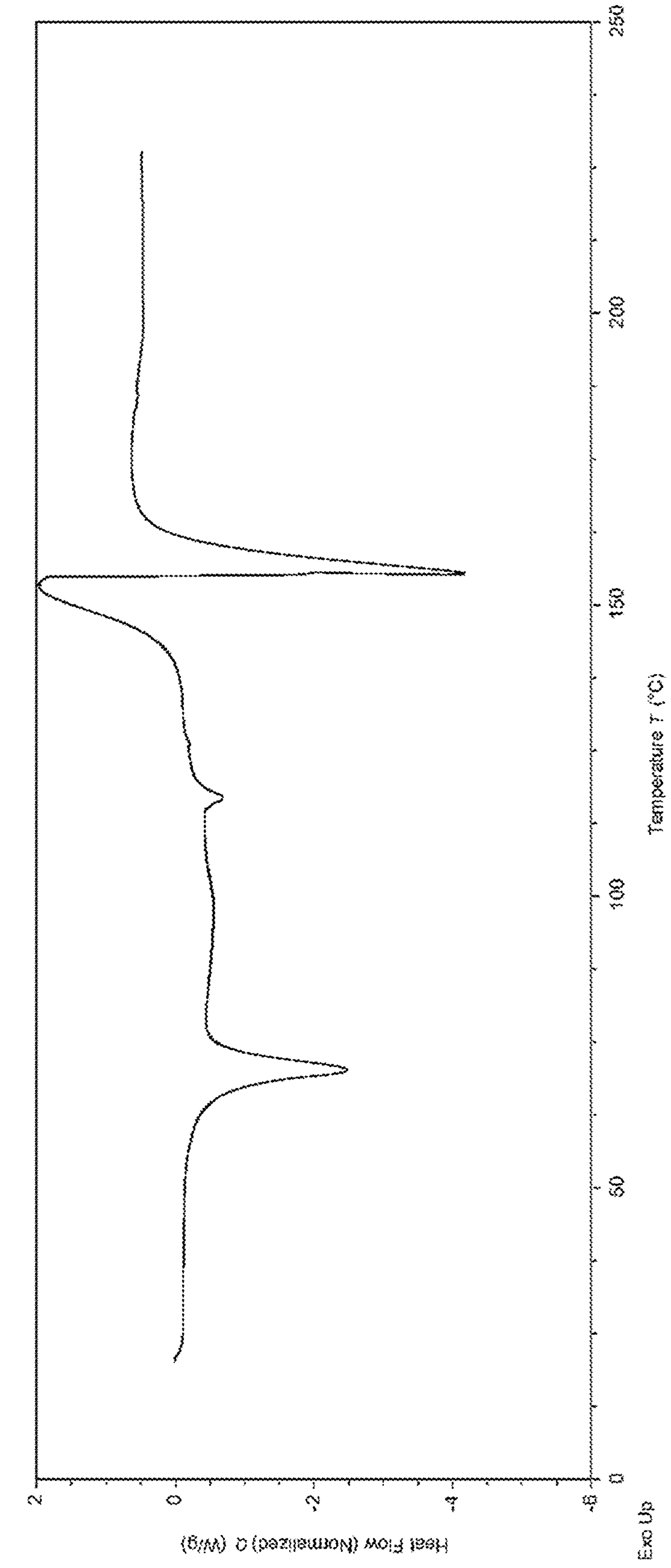
FIG. 3 shows the DSC pattern of NMNH disodium salt crystal form A.

The DSC pattern of crystal form A is substantially shown in FIG. 3, with heat absorption peaks in the range of 50° C.-80° C.

Example 2. Kilogram Scale-Up and Purification Effect of Crystal Form A

Preparation of NMNH disodium salt aqueous solution: To 10 liters of saturated sodium bicarbonate aqueous solution was added 1.7 Kg β-NMN, 0.94 Kg $Na_2S_2O_4$, and it was stirred overnight at room temperature, filtered to get the clear solution, adjusted the pH of the clear solution to 10 with NaOH, to get the NMNH disodium salt aqueous solution (HPLC purity of 95.2%).

At 20-40° C., the NMNH disodium salt aqueous solution was mechanically stirred, concentrated under reduced pressure, and concentrated to remove part of the water, and then 10 g of crystals (crystal form A) made in Example 1 were added. The solution continued to be concentrated under reduced pressure until the 1.5-2 liters remained, stopped being concentrated, cooled down to 0-10° C., filtered, and blown dry to obtain 2.07 Kg of NMNH disodium salt crystals, with a moisture (KF) of 26% and an HPLC purity of 99.4%; the resulting crystals were crystal form A of the compound of formula (I).

TABLE 2 purification effect of crystal form A
purification effect of Crystal form A

| Initial aqueous solution purity (HPLC, % area) | Compound | Product Purity (HPLC, % area) | Increased Percentage point in purity |
|---|---|---|---|
| 95.2 | Crystal form A | 99.4 | 4.2 |
| | Amorphous (freeze-dried) | 95.2 | 0 |

As can be seen from Table 2, crystal form A has some purification effect, while the amorphous solid obtained by lyophilization has no purification effect.

Example 3. Preparation of Crystal Form B 50 g of NMNH disodium salt crystals (crystal form A) prepared in Example 2 were weighed and dried in vacuum for 2-4 hours. The resulting solid crystal form was crystal form B of the compound of formula (I) with moisture (KF) of 16%.

Figure 4:
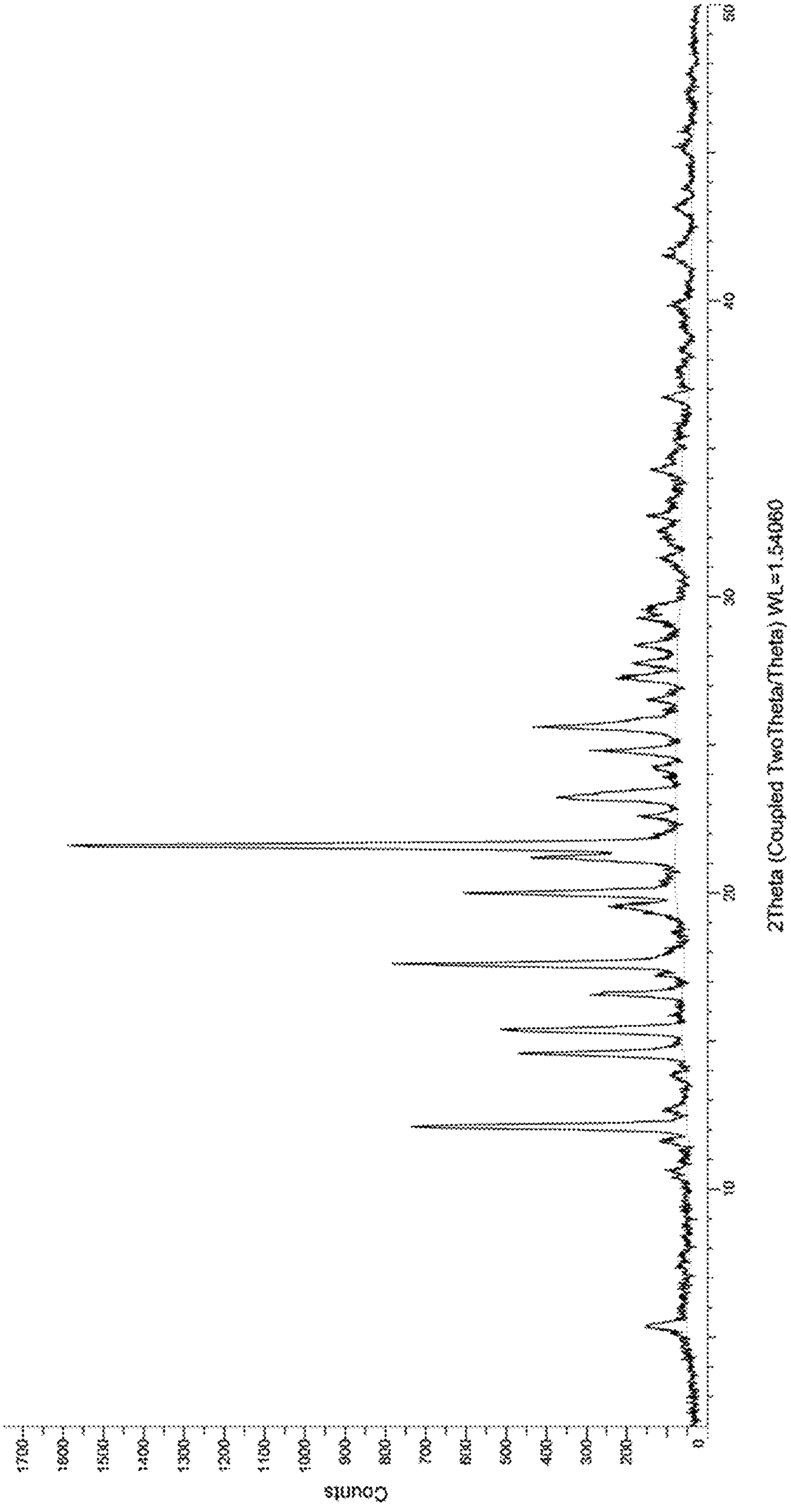
FIG. 4 shows the XRPD pattern of NMNH disodium salt crystal form B.

X-ray powder diffraction tests were carried out on the resulting solid, and the XRPD pattern of the resulting crystal form B is substantially as shown in FIG. 4, and the diffraction angle data is substantially as shown in Table 3 below, where the error range of the 2θ value is ±0.2°.

TABLE 3

XRPD data for crystal form B

| 2θ (°) | d(Å) | Relative intensity |
|---|---|---|
| 5.24 | 16.85167 | 6.3% |
| 7.67 | 11.52255 | 1.5% |
| 10.54 | 8.38280 | 3.5% |
| 11.51 | 7.67935 | 5.0% |
| 12.00 | 7.36830 | 46.3% |
| 12.57 | 7.03682 | 3.3% |
| 13.73 | 6.44280 | 2.4% |
| 14.47 | 6.11497 | 27.7% |
| 15.27 | 5.79614 | 28.5% |
| 16.50 | 5.36993 | 13.4% |
| 17.13 | 5.17063 | 3.3% |
| 17.49 | 5.06592 | 45.8% |
| 18.52 | 4.78703 | 1.7% |
| 19.44 | 4.56198 | 10.8% |
| 19.89 | 4.46104 | 35.0% |
| 21.09 | 4.20861 | 24.2% |
| 21.49 | 4.13220 | 100.0% |
| 22.47 | 3.95325 | 4.8% |
| 23.12 | 3.84370 | 20.1% |
| 24.10 | 3.68915 | 3.7% |
| 24.69 | 3.60264 | 11.7% |
| 25.50 | 3.49004 | 23.7% |
| 26.42 | 3.37086 | 4.1% |
| 27.15 | 3.28127 | 9.2% |
| 27.65 | 3.22330 | 7.5% |
| 28.26 | 3.15589 | 7.0% |
| 29.16 | 3.06029 | 6.4% |
| 29.45 | 3.03050 | 5.9% |

TABLE 3-continued

| XRPD data for crystal form B | | |
|---|---|---|
| 2θ (°) | d(Å) | Relative intensity |
| 31.19 | 2.86497 | 3.7% |
| 32.12 | 2.78456 | 3.8% |
| 32.62 | 2.74265 | 4.0% |
| 34.19 | 2.62061 | 5.3% |
| 35.15 | 2.55124 | 1.4% |
| 36.64 | 2.45060 | 4.2% |
| 38.25 | 2.35109 | 1.2% |
| 39.73 | 2.26698 | 3.8% |
| 41.39 | 2.17972 | 2.9% |
| 43.04 | 2.09971 | 2.9% |
| 45.09 | 2.00917 | 3.2% |
| 45.66 | 1.98535 | 1.3% |

Figure 5:
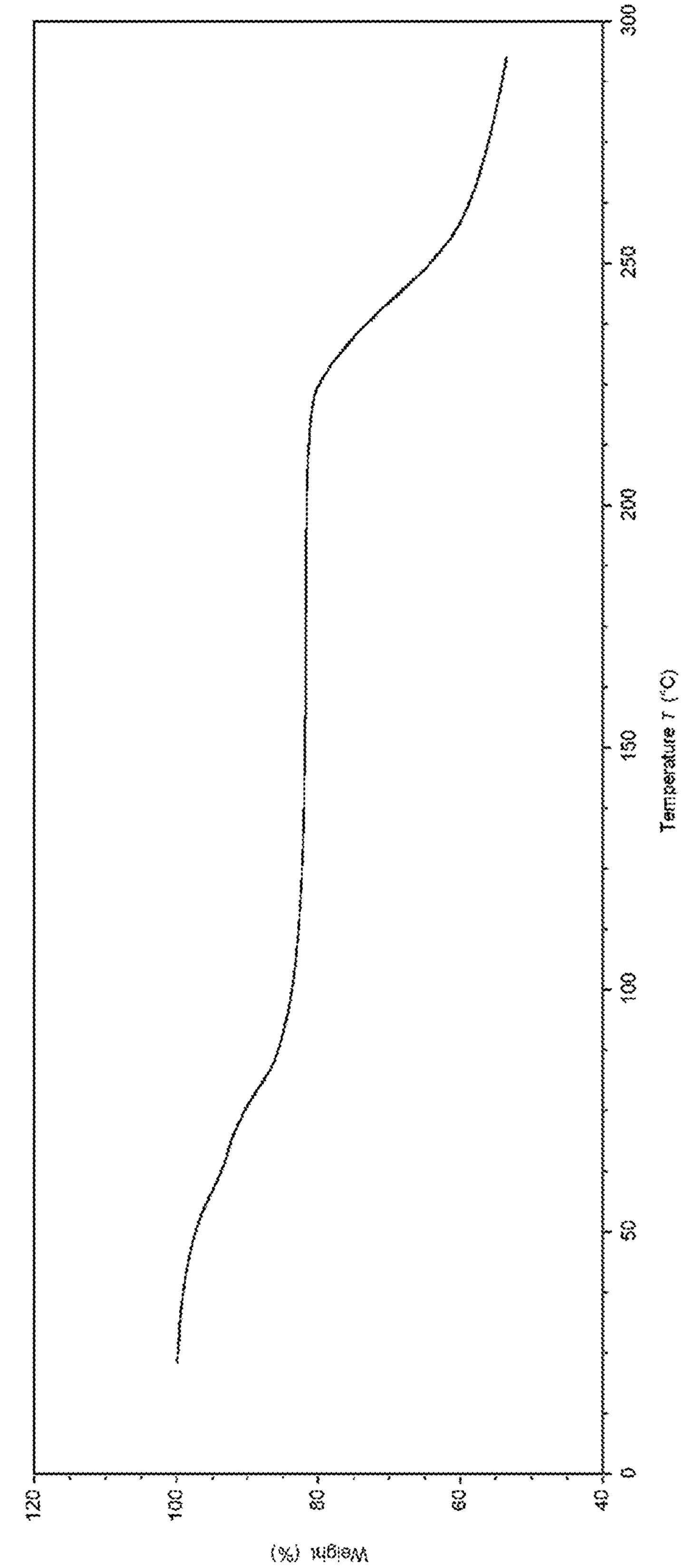
FIG. 5 shows the TGA pattern of NMNH disodium salt crystal form B.

The TGA pattern of crystal form B is substantially as shown in FIG. 5, with a weight loss of 120%-23% at 15° C.-200° C.

Figure 6:
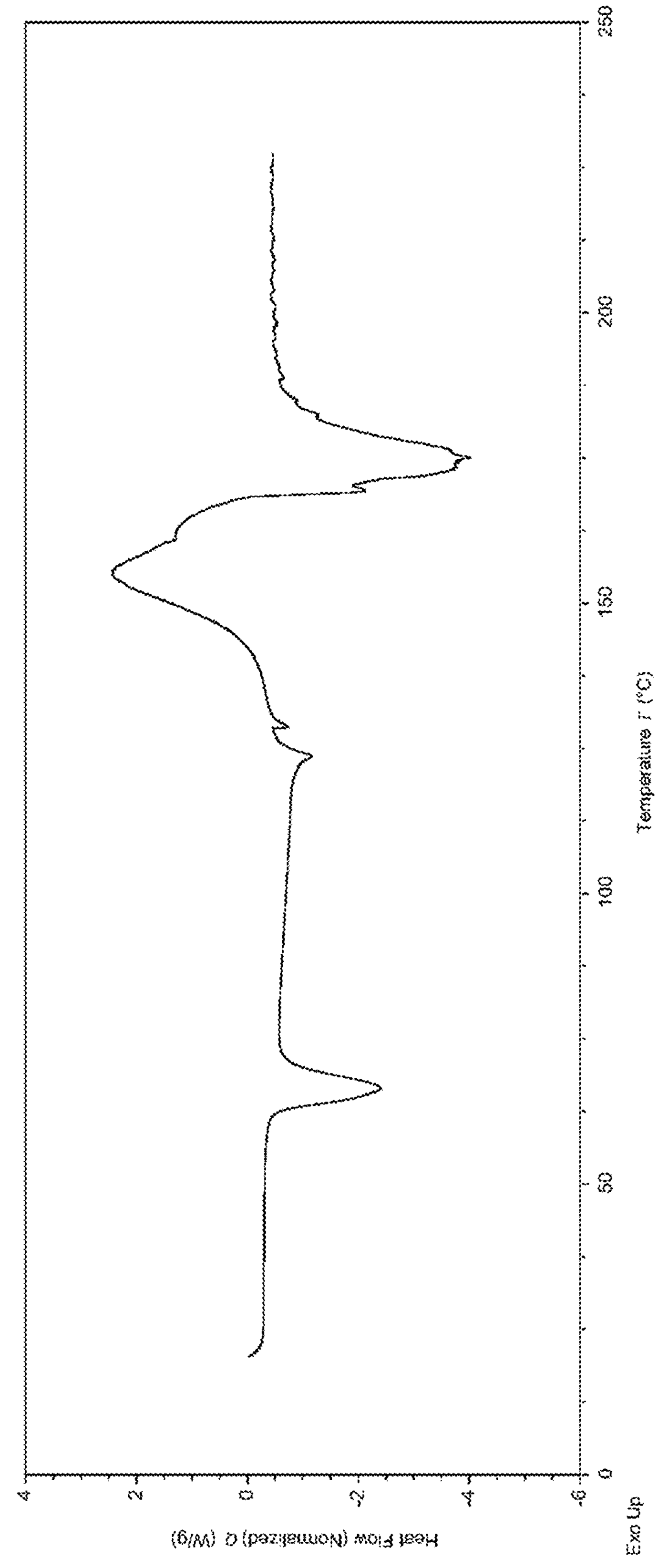
FIG. 6 shows the DSC pattern of NMNH disodium salt crystal form B.

The DSC pattern of crystal form B is substantially shown in FIG. 6, with heat absorption peaks in the range of 50° C.-80° C.

Example 4. Preparation of Crystal Form C 20 g of NMNH disodium salt crystals (crystal form B) prepared in Example 3 were weighed and dried in vacuum for 10-20 hours. The resulting solid crystal form was crystal form C of the compound of formula (I) with a moisture (KF) of 11%.

Figure 7:
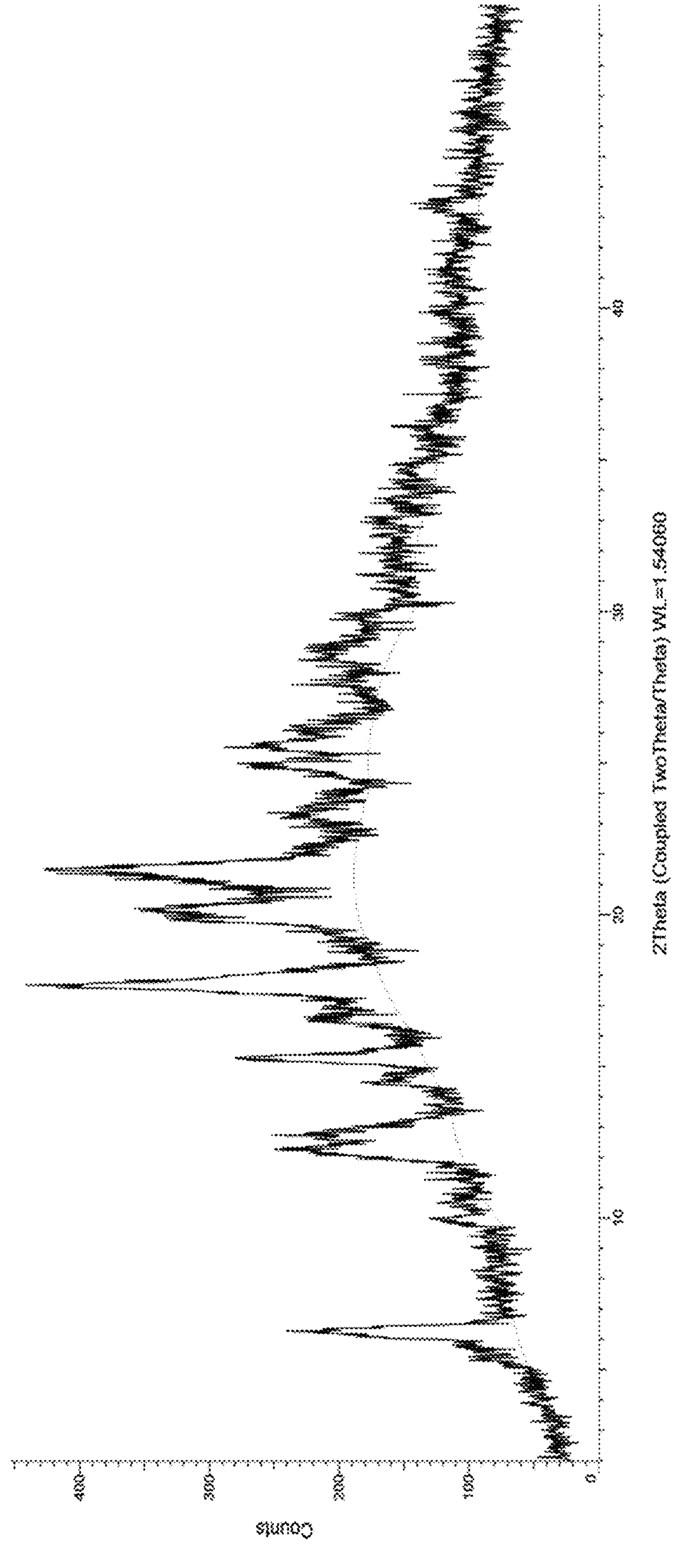
FIG. 7 shows the XRPD pattern of NMNH disodium salt crystal form C.

X-ray powder diffraction tests were carried out on the resulting solid, and the XRPD pattern of the resulting crystalline C is substantially as shown in FIG. 7, and the diffraction angle data is substantially as shown in Table 4 below, where the error range of the 2θ value is ±0.2°.

TABLE 4

| XRPD data for crystal form C | | |
|---|---|---|
| 2θ (°) | d(Å) | Relative intensity |
| 6.26 | 14.10620 | 59.0% |
| 9.98 | 8.85337 | 18.9% |
| 12.13 | 7.29278 | 39.8% |
| 12.28 | 7.20286 | 39.8% |
| 12.77 | 6.92824 | 40.2% |
| 15.29 | 5.79145 | 53.2% |
| 16.57 | 5.34585 | 21.0% |
| 17.68 | 5.01188 | 100.0% |
| 19.90 | 4.45836 | 51.9% |
| 20.19 | 4.39421 | 60.2% |
| 21.49 | 4.13223 | 86.1% |
| 23.28 | 3.81768 | 20.2% |
| 24.91 | 3.57143 | 32.4% |
| 25.57 | 3.48047 | 31.6% |
| 33.69 | 2.65794 | 11.9% |

Figure 8:
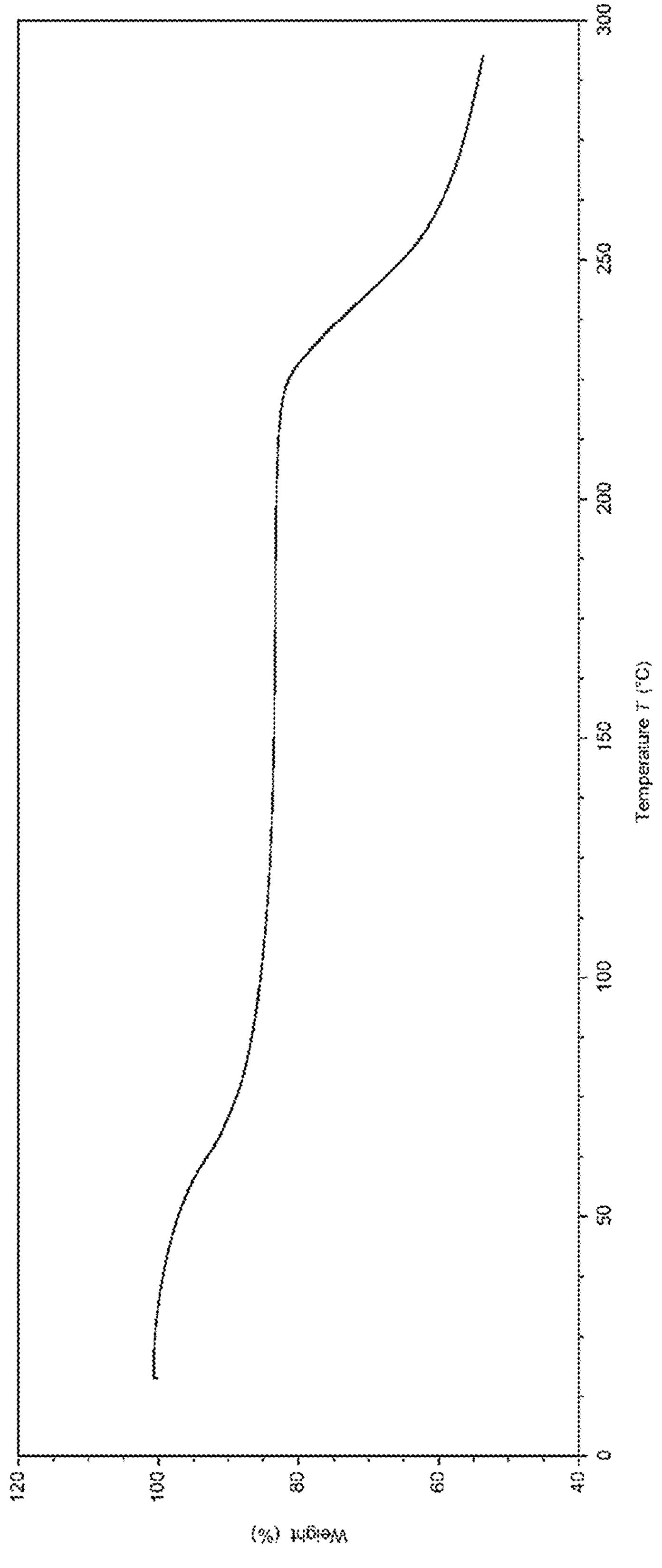
FIG. 8 shows the TGA pattern of NMNH disodium salt crystal form C.

The TGA pattern of crystal form C is substantially as shown in FIG. 8, with a weight loss of 8%-16% at 15° C.-200° C.

Figure 9:
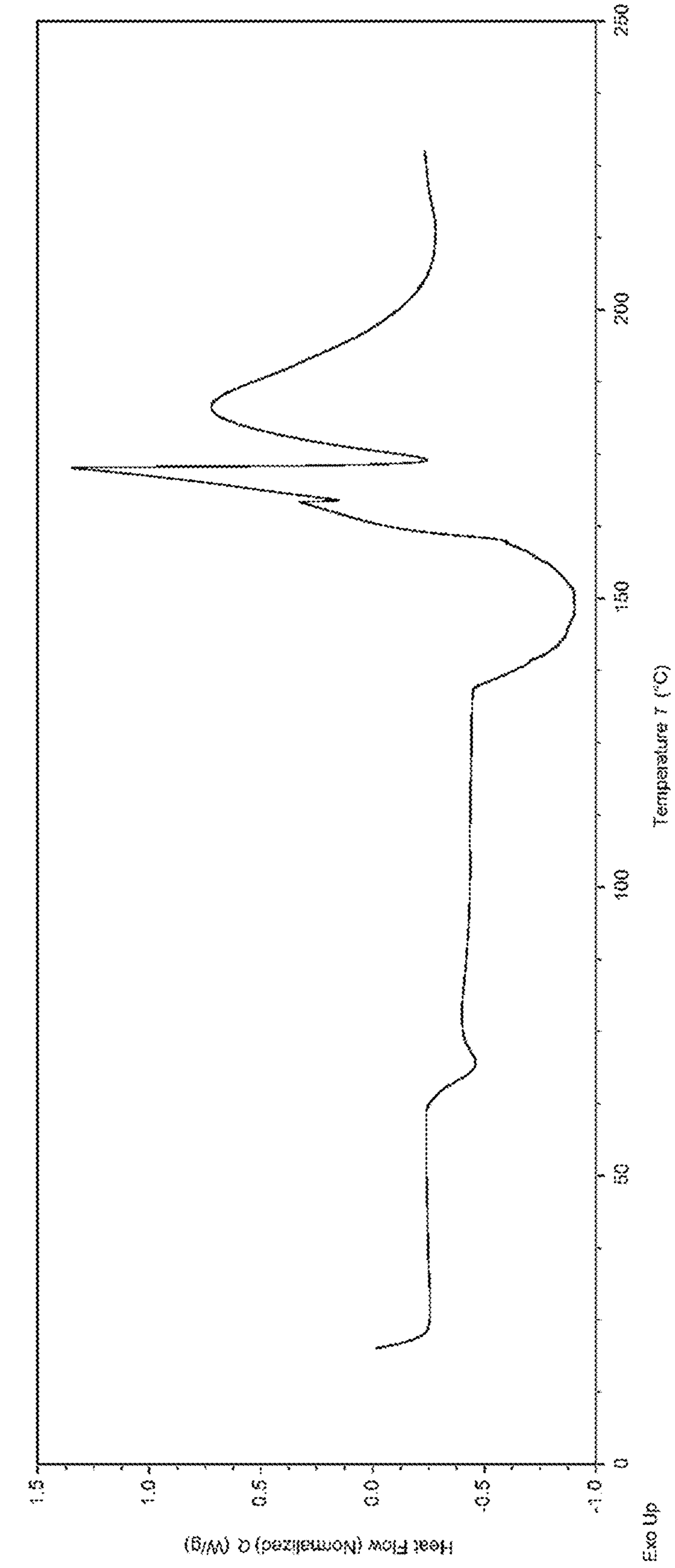
FIG. 9 shows the DSC pattern of NMNH disodium salt crystal form C.

The DSC pattern of crystal form C is substantially shown in FIG. 9, with heat absorption peaks in the range of 50° C.-80° C.

Example 5. Crystal Form B Transforms into Crystal Form A by Absorpting Water from the Air 1 g of NMNH disodium salt crystals (crystal form B) made in Example 3 was weighed and exposed in air at 2-8° C. with an air relative humidity of 70-80%, and the resulting solid crystal form was crystal form A of the compound of formula (I) after 30 days, with a moisture (KF) of 29%.

Example 6. Crystal Form C Transforms into Crystal Form a by Absorpting Water from the Air 1 g of NMNH disodium salt crystals (crystal form C) prepared in Example 4 was weighed and exposed in air at 2-8° C. with an air relative humidity of 70-80%, and the resulting solid crystal form was crystal form A of the compound of formula (I) after 24 hours, with a moisture (KF) of 24%.

Example 7. Preparation of Amorphous Solids of Compounds of Formula (I)

30 g of NMNH disodium salt crystals prepared in Example 2 were weighed and dissolved in 90 ml of water to obtain a clarified solution, which was freezed to a solid and then freeze-dried. The product obtained after 24 hours of lyophilization was an amorphous solid, which was foamy and had poor fluidity and a moisture (KF) of 9%.

Figure 10:
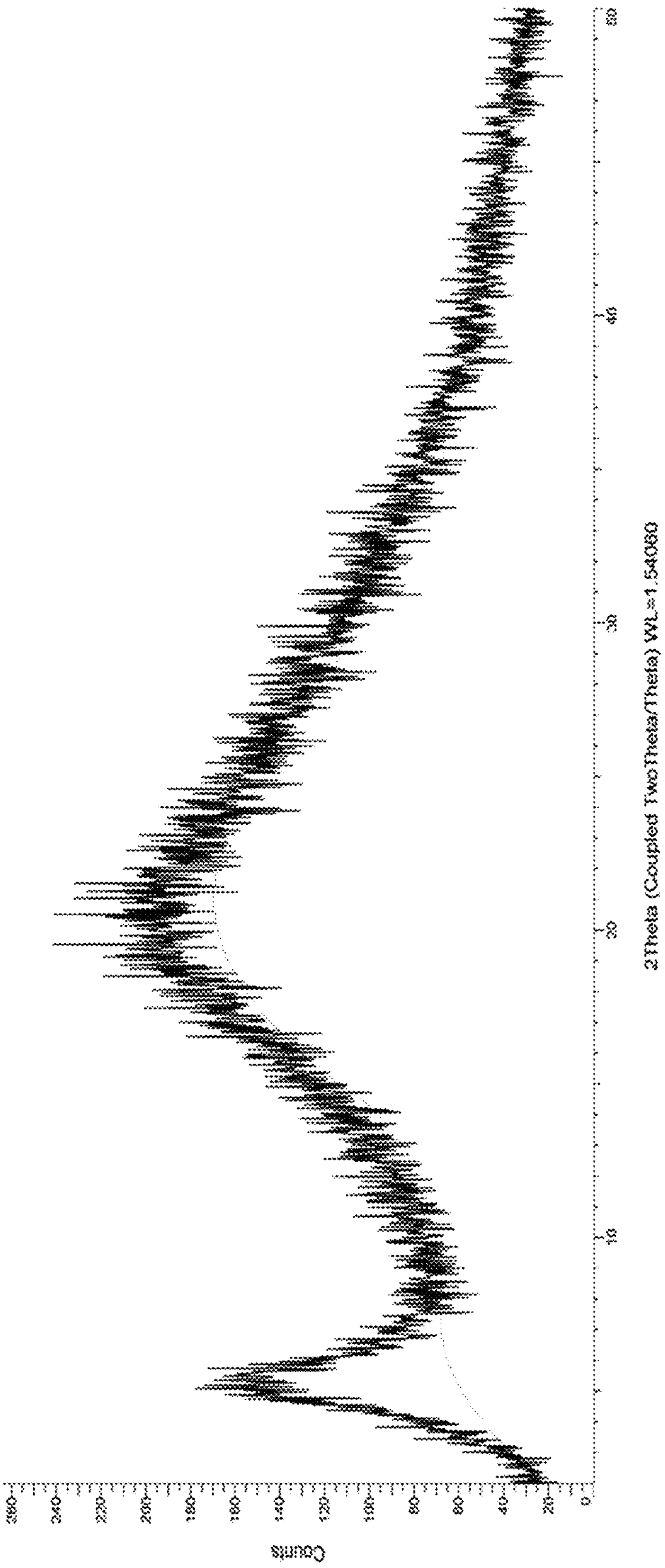
FIG. 10 shows the XRPD pattern of the amorphous NMNH disodium salt.

The resulting amorphous solid was subjected to X-ray powder diffraction test and its XRPD pattern is substantially as shown in FIG. 10.

Figure 11:
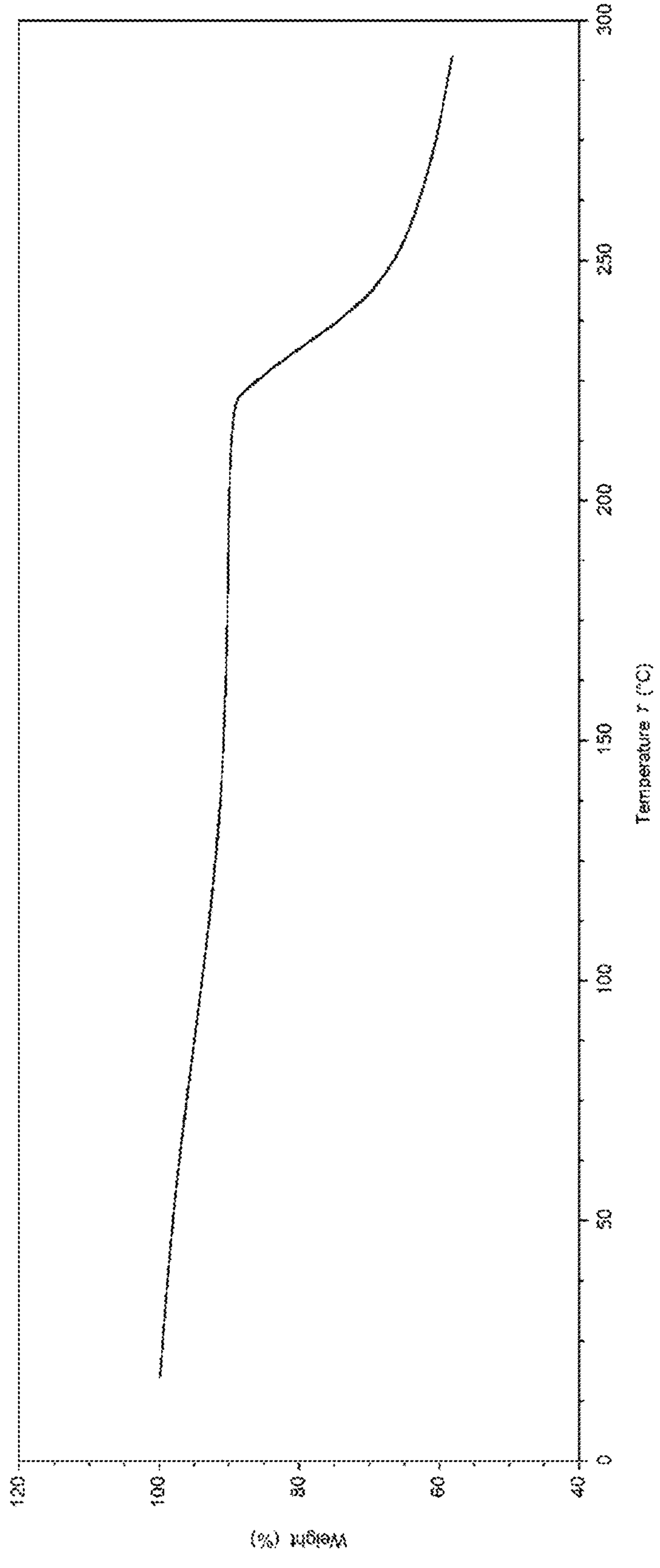
FIG. 11 shows the TGA pattern of the amorphous NMNH disodium salt.

The TGA pattern of the amorphous solid is substantially as shown in FIG. 11, with 1%-15% weight loss at 15° C.-200° C.

Figure 12:
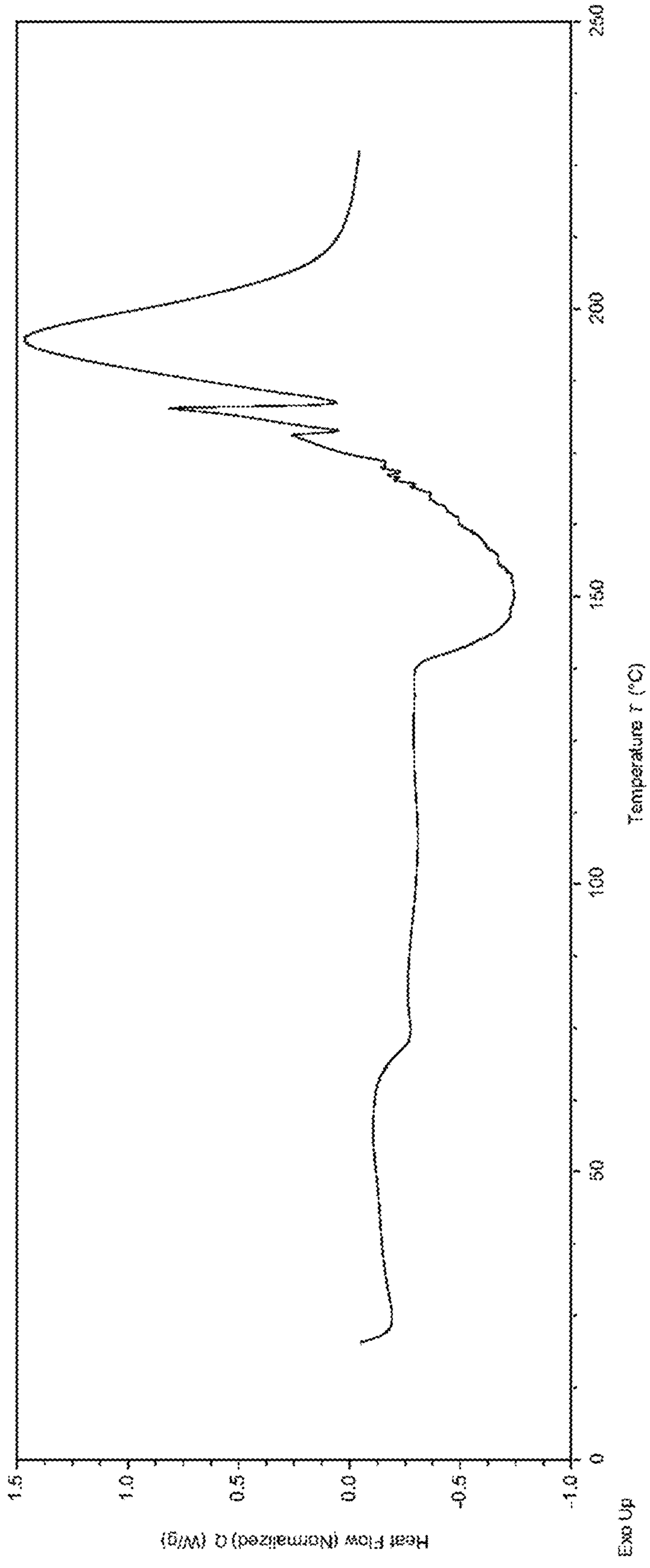
FIG. 12 shows the DSC pattern of the amorphous NMNH disodium salt.

The DSC pattern of the amorphous solid is substantially as shown in FIG. 12, with heat absorption peaks in the range of 50° C.-80° C.

Example 8. Stability of Crystal Form A Vs. Amorphous Solids (1) The product crystals (crystal form A) in Example 2 and the product amorphous solids in Example 7 were both placed openly in a stability chamber at 25° C. and 65% RH to examine the stability, and the data as shown in Table 5 and FIG. 14 were obtained.

TABLE 5

| Stability of crystal form A vs. amorphous solids (25° C., 65% RH) | | |
|---|---|---|
| | NMNH disodium salt purity (HPLC, % area) | |
| Time | Crystal form A | Amorphous Solids |
| 0 day | 99.33 | 99.30 (powders) |
| 1 day | 99.27 | 99.02 (oil) |
| 5 day | 99.01 | / |

Figure 14:
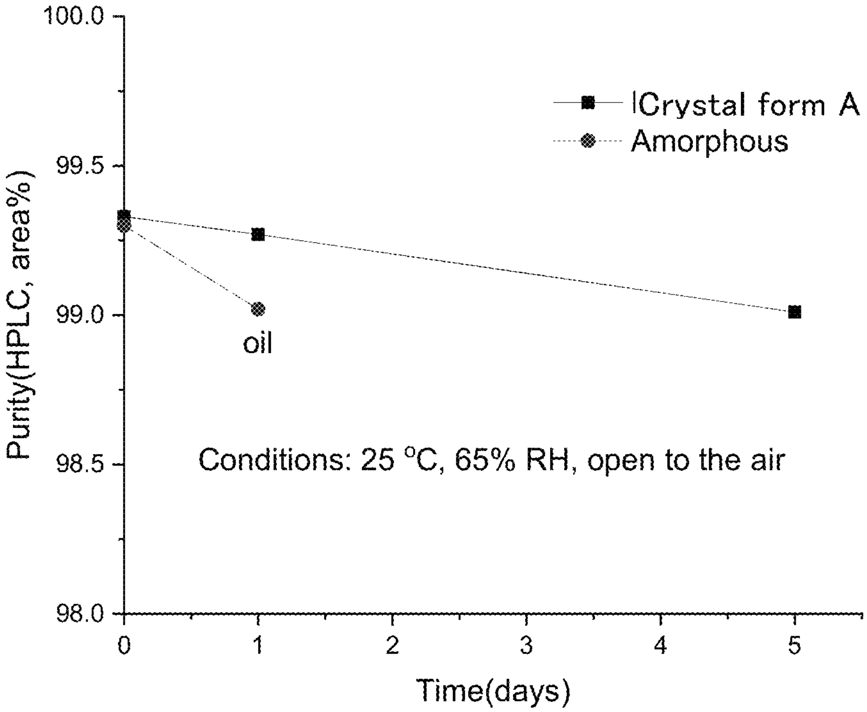
FIG. 14 shows the stability of crystal form A versus amorphous solids at 25° C. and 65% RH open-ended conditions.

As can be seen in Table 5 and FIG. 14, the purity of crystal form A decreased from 99.33% to 99.01% after 5 days of placement (still a crystal powder), while the purity of the amorphous solid decreased from 99.30% to 99.02% after 1 day of placement (the powder absorbed water and turned into an oil). It can be seen that the crystal form A solid of NMNH disodium salt is more stable than the amorphous solid.

Figure 15:
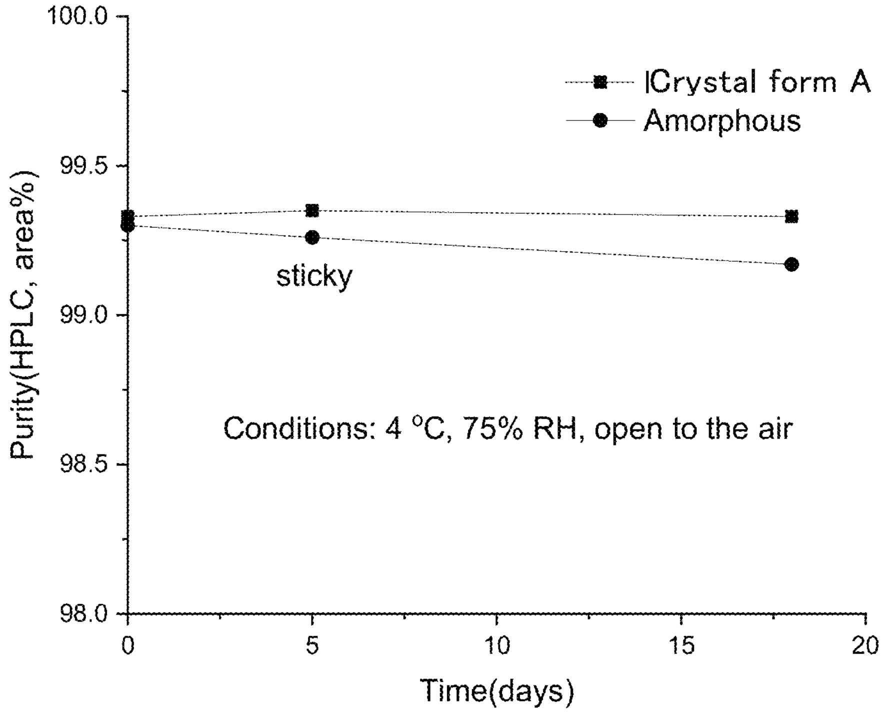
FIG. 15 shows the stability of crystalline type A versus amorphous solids at 4° C. and 75% RH open-ended conditions.

(2) The product crystals (crystal form A) in Example 2 and the product amorphous solids in Example 7 were both placed openly in a stability chamber at 4° C. and 75% RH to examine the stability, and the data as shown in Table 6 and FIG. 15 were obtained.

TABLE 6

| Stability of crystal form A vs. amorphous solids (4° C., 75% RH) | | |
|---|---|---|
| | NMNH disodium salt purity (HPLC, % area) | |
| Time | Crystal form A | Amorphous Solids |
| 0 day | 99.33 | 99.30 |
| 5 day | 99.35 | 99.26 |
| 18 day | 99.33 | 99.17 |

As can be seen from Table 6 and FIG. 15, the purity of crystal form A was 99.33% after 18 days of placement, almost unchanged (still a crystal powder), while the purity of the amorphous solid decreased from 99.30% to 99.26% after 5 days of placement (the powder solid absorbed water and became viscous to form a mass), and the purity decreased to 99.17% on the 18th day (the color became darker). This shows that the crystal form A solid of NMNH disodium salt is more stable than the amorphous solid.

All documents referred to in this invention are cited as references in this application as if each document were cited individually as a reference. It is further to be understood that after reading the foregoing teachings of the present invention, a person skilled in the art may make various alterations or modifications to the present invention, and these equivalent forms will likewise fall within the scope of the claims appended to this application.

The invention claimed is:

1. A crystal of a reduced β-nicotinamide mononucleotide disodium salt of formula (I), wherein the crystal is a hydrate of reduced β-nicotinamide mononucleotide disodium salt, and crystal form of the crystal is crystal form A, crystal form B or crystal form C, (I)

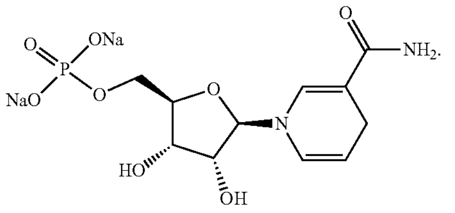

wherein the XRPD pattern of the crystal form A comprises 5 or more 20 values selected from the group consisting of: 12.7°±0.2°, 15.9°±0.2°, 18.0°=0.2°, 20.4°±0.2°, 20.9°=0.2°, and 31.8°±0.2°; the XRPD pattern of the crystal form B comprises 5 or more 20 values selected from the group consisting of: 12.0°±0.2°, 14.5°=0.2°, 15.3°±0.2°, 17.5°±0.2°, 19.9°±0.2°, and 21.5°±0.2°; and the XRPD pattern of the crystal form C comprises 5 or more 20 values selected from the group consisting of: 6.3°±0.2°, 15.3°±0.2°, 17.7°±0.2°, 19.9°±0.2°, 20.2°±0.2°, and 21.5°=0.2°.

2. The crystal of the reduced β-nicotinamide mononucleotide disodium salt according to claim 1, wherein the XRPD pattern of the crystal form A further comprises 1 or more 20 values selected from the group consisting of: 10.5°±0.2°, 19.8°±0.2°, 22.6°±0.2°, 24.0°±0.2°, 26.1°±0.2°, 28.7°±0.2°, 30.8°±0.2°, and 33.4°±0.2°.

3. The crystal of the reduced β-nicotinamide mononucleotide disodium salt according to claim 1, wherein the crystal form A further has one or more features selected from the following group:

1) the XRPD pattern of the crystal form A comprises the following 20 values: 5.0°±0.2°, 10.5°=0.2°, 12.7°=0.2°, 13.7°±0.2°, 14.9°±0.2°, 15.9°±0.2°, 16.1°=0.2°, 16.6°=0.2°, 18.0°=0.2°, 19.8°±0.2°, 20.4°±0.2°, 20.9°±0.2°, 22.6°±0.2°, 24.0°±0.2°, 24.7°±0.2°, 25.2°±0.2°, 25.7°±0.2°, 26.1°±0.2°, 27.8°=0.2°, 28.7°=0.2°, 29.3°±0.2°, 30.3°=0.2°, 30.8°=0.2°, 31.8°=0.2°, 32.7°=0.2°, 33.4°=0.2°, 34.2°±0.2°, 35.8°±0.2°, 36.4°±0.2°, 37.4°±0.2°, 39.7°±0.2°, 41.2°±0.2°, 41.7°±0.2°, 42.6°±0.2°, 43.9°±0.2°, 44.3°±0.2°, 46.0°±0.2°, 46.4°±0.2°, and 49.2°±0.2°;

2) the TGA pattern of the crystal form A has a weight loss of 19%-30% at 15° C.-200° C.;

3) the DSC pattern of the crystal form A has a heat absorption peak in the range of 50° C.-80° C.

4. The crystal of the reduced β-nicotinamide mononucleotide disodium salt according to claim 1, wherein the crystal form A further has one or more features selected from the following group:

1) the XRPD pattern of the crystal form A is substantially as characterized in FIG. 1;

2) the TGA pattern of the crystal form A is substantially as characterized in FIG. 2;

3) the DSC pattern of the crystal form A is substantially as characterized in FIG. 3.

5. The crystal of the reduced β-nicotinamide mononucleotide disodium salt according to claim 1, wherein the crystal form B has one or more features selected from the following group:

1) the XRPD pattern of the crystal form B further comprises 1 or more 20 values selected from the group consisting of: 21.1°±0.2°, 23.1°±0.2°, and 25.5°±0.2°;

2) the TGA pattern of the crystal form B has a weight loss of 12%-23% at 15° C.-200° C.;

3) the DSC pattern of the crystal form B has a heat absorption peak in the range of 50° C.-80° C.

6. The crystal of the reduced β-nicotinamide mononucleotide disodium salt according to claim 1, wherein the crystal form B has one or more features selected from the following group:

1) the XRPD pattern of the crystal form B is substantially as characterized in FIG. 4;

2) the TGA pattern of the crystal form B is substantially as characterized in FIG. 5; and 3) the DSC pattern of the crystal form B is substantially as characterized in FIG. 6.

7. The crystal of the reduced β-nicotinamide mononucleotide disodium salt according to claim 1, wherein the XRPD pattern of the crystal form B comprises the following 2θ values:

5.2°=0.2°, 7.7°±0.2°, 10.5°=0.2°, 11.5°=0.2°, 12.0°±0.2°, 12.6°±0.2°, 13.7°±0.2°, 14.5°±0.2°, 15.3°±0.2°, 16.5°±0.2°, 17.1°±0.2°, 17.5°±0.2°, 18.5°±0.2°, 19.4°±0.2°, 19.9°±0.2°, 21.1°±0.2°, 21.5°=0.2°, 22.5°=0.2°, 23.1°=0.2°, 24.1°±0.2°, 24.7°±0.2°, 25.5°±0.2°, 26.4°±0.2°, 27.2°=0.2°, 27.7°=0.2°, 28.3°=0.2°, 29.2°=0.2°, 29.5°±0.2°, 31.2°±0.2°, 32.1°±0.2°, 32.6°±0.2°, 34.2°±0.2°, 35.1°±0.2°, 36.6°=0.2°, 38.3°=0.2°, 39.7°=0.2°, 41.4°±0.2°, 43.0°±0.2°, 45.1°±0.2°, and 45.7°±0.2°.

8. The crystal of the reduced β-nicotinamide mononucleotide disodium salt according to claim 1, wherein the crystal form C has one or more features selected from the following group:

1) the XRPD pattern of the crystal form C further comprises 1 or more 20 values selected from the group consisting of: 6.3°±0.2°, 10.0°±0.2°, 12.1°±0.2°, 12.3°±0.2°, 12.8°±0.2°, 15.3°±0.2°, 16.6°±0.2°, 17.7°±0.2°, 19.9°=0.2°, 20.2°=0.2°, 21.5°=0.2°, 23.3°=0.2°, 24.9°=0.2°, 25.6°±0.2°, and 33.7°=0.2°;

2) the TGA pattern of the crystal form C has a weight loss of 8%-16% at 15° C.-200° C.;

3) the DSC pattern of the crystal form C has a heat absorption peak in the range of 50° C.-80° C.

9. The crystal of the reduced β-nicotinamide mononucleotide disodium salt according to claim 1, wherein the crystal form C has one or more features selected from the following group:

1) the XRPD pattern of the crystal form C is substantially as characterized in FIG. 7;

2) the TGA pattern of the crystal form C is substantially as characterized in FIG. 8; and 3) the DSC pattern of the crystal form C is substantially as characterized in FIG. 9.

10. A method for preparing the crystal of reduced β-nicotinamide mononucleotide disodium salt according to claim 1, wherein the method comprises the following steps:

1) Adding the reduced β-nicotinamide mononucleotide disodium salt to water to obtain a water solution containing reduced β-nicotinamide mononucleotide disodium salt;

2) under stirring conditions, purging the solution with nitrogen, and crystallizing to obtain the crystal form A according to claim 1; alternatively, under stirring conditions, adding the crystal form A to the solution was as a crystalline seed and concentrating under reduced pressure, and crystallizing to obtain the crystal form A according to claim 1.

11. A method for preparing the crystal of reduced β-nicotinamide mononucleotide disodium salt according to claim 10, wherein crystal form is crystal form B, and the method further comprises the following step: subjecting the crystal form A to vacuum drying transcrystallization to obtain the crystal form B.

12. A method for preparing the crystal of reduced β-nicotinamide mononucleotide disodium salt according to claim 10, wherein crystal form is crystal form C, and the method further comprises the following step: subjecting the crystal form B to vacuum drying transcrystallization to obtain the crystal form C.

13. A composition, comprising: (a) the crystal according to claim 1, and (b) pharmaceutically acceptable excipients, or acceptable excipients for cosmetic.

14. A method of preparation of a drug or a cosmetic, comprising providing the crystal of claim 1 as an active ingredient.

* * * * *